US006436897B2

(12) United States Patent
Danko et al.

(10) Patent No.: US 6,436,897 B2
(45) Date of Patent: Aug. 20, 2002

(54) PHARMACEUTICAL FORMULATIONS FOR IGF/IGFBP

(75) Inventors: Stephen Danko, San Francisco; David Passmore, Menlo Park; Yasushi Ogawa, Pacifica, all of CA (US)

(73) Assignee: Celtrix Pharmaceuticals, Inc., Glen Allen, VA (US)

( * ) Notice: Subject to any disclaimer, the term of this patent is extended or adjusted under 35 U.S.C. 154(b) by 0 days.

(21) Appl. No.: 09/089,062

(22) Filed: Jun. 1, 1998

(51) Int. Cl.$^7$ ............................................... A61K 38/30
(52) U.S. Cl. ................................ 514/2; 514/3; 514/12; 530/303
(58) Field of Search ...................... 514/2, 12, 3; 530/303

(56) References Cited

U.S. PATENT DOCUMENTS

| | | | | |
|---|---|---|---|---|
| 5,643,867 A | * | 7/1997 | Maack | 514/3 |
| 5,681,814 A | | 10/1997 | Clark et al. | 514/12 |
| 5,723,441 A | * | 3/1998 | Higley | 514/12 |
| 5,948,757 A | * | 9/1999 | Sommer | 514/12 |

FOREIGN PATENT DOCUMENTS

| | | | | |
|---|---|---|---|---|
| WO | WO 95/04076 | 2/1995 | | C07K/14/705 |
| WO | WO 95/08567 | 3/1995 | | |
| WO | WO 95/13823 | 5/1995 | | |
| WO | WO 96/40722 | 12/1996 | | C07H/21/04 |
| WO | WO 96/40736 | 12/1996 | | C07K/1/14 |
| WO | WO96/40736 | * 12/1996 | | |
| WO | WO 97/07816 | * 3/1997 | | |
| WO | WO 98/06423 | 2/1998 | | |

OTHER PUBLICATIONS

Arai, The Journal of Biological Chemistry 269 (32):20388–20393, 1994.*
Adams et al., "Pharmacokinetics and Bioavailability of rhIGF–I/IGFBP–3 in the Rat and Monkey" *Prog. Growth Factor Res.* (1996) 6:2–4:347–356.
Arai et al. "Heparin, Heparan Sulfate, and Dermatan Sulfate Regulate Formation of the Insulin–like Growth Factor–I and Insulin–like Growth Factor–binding Protein Complexes" *J. of Bio. Chem.* (1994) 269(32):20388–20393.
Bagi et al. "Benefit of Systemically Administered rhIGF–I and rhIGF–I/IGFBP–3 on Cancellous Bone in Ovariectomized Rats" *J. Bone Mineral Res.* (1994) 9(8):1301–1311.
Barreca et al. "Functions And Regulation Of The Acid–Labile Subunit Of The 150 K Complex" *Prog. in Grow. Fact. Res.* (1995) 6(2–4):231–239.
Baxter et al. "Binding Proteins For Insulin–Like Growth Factors In Adult Rat Serum, Comparison With Other Human And Rat Binding Proteins" *Biochem. & Biophys. Res. Comm.* (1987) 147(1):408–415.
Baxter et al. "High Molecular Weight Insulin–like Growth Factor Binding Protein Complex" *J. Biol. Chem.*(1989) 264(20):11843–11848.

Baxter, Robert C. "Characterization of the Acid–Labile Subunit of the Growth Hormone–Dependent Insulin–Like Growth Factor Binding Protein Complex" *J. Clin. Endocrinol. Metab* (1988) 67:265–272.
Baxter, Robert C. "The Insulin–like Growth Factors and Their Binding Proteins" *Comp. Biochem. Physiol.* (1988) 91B(2):229–235.
Blum et al. (1991), "Plasma IGFBP–3 Levels as Clinical Indicators" *Modern Concepts of Insulin–Like Growth Factors*, pp. 381–393, E.M. Spencer, ed., Elsevier, New York.
Cooke et al. "Solution Structure of Human Insulin–Like Growth Factor 1: A Nuclear Magnetic Resonance and Restrained Molecular Dynamics Study" *Biochem.* (1991) 30(22):5484–5491.
Fransson et al. "Solution Effects on the Solubility and Physical Stability of Human Insulin–Like Growth Factor I" *Pharm. Res.* (1997) 14(5):606–612.
Lee et al. "Purified Rat Acid–Labile Subunit and Recombinant Human Insulin–Like Growth Factor (IGF)–Binding Protein–3 Can Form a 150–Kilodalton Binary Complex in Vitro in the Abscence of IGFs" *Endocrin.* (1995) 136:4982–4989.
Martin et al. "Insulin–like Growth Factor–binding Protein from Human Plasma" *J. of Bio. Chem.* (1986) 261(19)8754–8760.
Rinderknecht et al. "The Amino Acid Sequence of Human Insulin–like Growth Factor I and Its Structural Homology with Proinsulin" *J. of Bio. Chem.* (1978) 253(8):2769–2776.
Sato et al. "Three–Dimensional Structure of Human Insulin–Like Growth Factor–I (IGF–I) Determined by $_1$H–NMR and Distance Geometry" *Int. J. Peptide Protein Res.* (1993) 41:433–440.
Sommer et al. "Molecular Genetics and Actions of Recombinant Insulin–like Growth Factor Binding Protein–3" *Modern Concepts of Insulin–Like Growth Factors* (1991) pp. 715–728, E.M. Spencer, ed., Elsevier, New York.
Spratt et al. "Cloning and Expression of Human Insulin–Like Growth Factor Binding Protein 3" *Growth Factors* (1990) 3:63–72.
Tressel et al. "Purification and Characterization of Human Recombinant Insulin–like Growth Factor Binding Protein 3 Expressed in Chinese Hamster Ovary Cells" *Biochem. & Biophys.Res. Comm.* (1991) 178(2):625–633.
USP (United States Pharmacopeia) United States Pharmacopeial Convention, Inc., Rockville, MD, 1995.
Wood et al. "Cloning and Expression of the Growth Hormone–Dependent Insulin–Like Growth Factor–Binding Protein" *Mol. Endo.* (1988) 2(12):1176–1185.

* cited by examiner

*Primary Examiner*—Yvonne Eyler
*Assistant Examiner*—Eliane Lazar-Wesley
(74) *Attorney, Agent, or Firm*—Foley & Lardner

(57) ABSTRACT

New pharmaceutical formulations for IGF/IGFBP complex are disclosed. IGF/IGFBP complex, preferably rhIGF-I/IGFBP-3 complex is formulated with bulking agents and optionally buffer salts, but without added osmolyte salts. Also disclosed are lyophilized formulations for IGF/IGFBP complex.

25 Claims, 1 Drawing Sheet

Figure 1

```
1                                                                    50
GASSAGLGPV  VRCEPCDARA  LAQCAPPPAV  CAELVREPGC  GCCLTCALSE 51                                                                  100
GQPCGIYTER  CGSGLRCQPS  PDEARPLQAL  LDGRGLCVNA  SAVSRLRAYL 101                                                                 150
LPAPPAPGNA  SESEEDRSAG  SVESPSVSST  HRVSDPKFHP  LHSKIIIIKK 151                                                                 200
GHAKDSQRYK  VDYESQSTDT  QNFSSESKRE  TEYGPCRREM  EDTLNHLKFL 201                                                                 250
NVLSPRGVHI  PNCDKKGFYK  KKQCRPSKGR  KRGFCWCVDK  YGQPLPGYTT 251            264
KGKEDVHCYS  MQSK
```

PHARMACEUTICAL FORMULATIONS FOR IGF/IGFBP

TECHNICAL FIELD

The invention relates generally to the field of formulation of therapeutic proteins, and particularly to formulations for complexes of insulin-like growth factor I (IGF-I) and insulin-like growth factor binding protein 3 (IGFBP-3).

BACKGROUND ART

Growth factors are polypeptides that stimulate a wide variety of biological responses (e.g. DNA synthesis, cell division, expression of specific genes, etc.) in a defined population of target cells. A number of different growth factor families have been identified, including the transforming growth factor beta family (TGF-βs), epidermal growth factor and transforming growth factor alpha (the TGF-αs), the platelet-derived growth factors (PDGFs), the fibroblast growth factor family (FGFs) and the insulin-like growth factor family (IGFs), which includes IGF-I and IGF-II.

IGF-I and IGF-II (the "IGFs") are related in amino acid sequence and structure, with each polypeptide having a molecular weight of approximately 7.5 kilodaltons (kDa). IGF-I mediates the major effects of growth hormone, and is thus the primary mediator of growth after birth. IGF-I has also been implicated in the actions of various other growth factors, since the treatment of cells with such growth factors leads to increased production of IGF-I. In contrast, IGF-II is believed to have a major role in fetal growth. Both IGF-I and IGF-II have insulin-like activities (hence their names), and are mitogenic (stimulate cell division) for cells in neural tissue.

Almost all IGF circulates in a non-covalently associated complex of IGF-I, insulin-like growth factor binding protein 3 (IGFBP-3) and a larger protein subunit termed the acid labile subunit (ALS), such that very little free IGF-I is detectable. The ternary complex is composed of equimolar amounts of each of the three components. ALS has no direct IGF-binding activity and appears to bind only to the IGF/IGFBP-3 complex (Baxter et al., *J. Biol. Chem.* 264(20):11843–11848, 1989), although some reports suggest that IGFBP-3 can bind to rat ALS in the absence of IGF (Lee et al., *Endocrinology* 136:4982–4989, 1995). The ternary complex of IGF/IGFBP-3/ALS has a molecular weight of approximately 150 kDa. This ternary complex is thought to act "as a reservoir and a buffer for IGF-I and IGF-II preventing rapid changes in the concentration of free IGF" (Blum et al. (1991), "Plasma IGFBP-3 Levels as Clinical Indicators" in MODERN CONCEPTS OF INSULIN-LIKE GROWTH FACTORS, pp. 381–393, E. M. Spencer, ed., Elsevier, N.Y.). While there is essentially no excess (unbound) IGFBP-3 in circulation, a substantial excess of free ALS does exist (Baxter, *J. Clin. Endocrinol. Metab.* 67:265–272, 1988).

The complex of IGF-I and IGFBP-3 ("binary complex" or "IGF-I/IGFBP-3") is considerably different from uncomplexed IGF-I, both physically and chemically. The binary complex is approximately 5 times larger than uncomplexed IGF-I, has a different overall pI, and has a different overall hydrophobicity. These differences cause the binary complex to behave quite differently than IGF-I.

Due to its wide range of activities, IGF-I has been developed as a treatment for a variety of conditions, including amyotrophic lateral sclerosis (commonly known as Lou Gehrig's disease) and diabetes. Unfortunately, the administration of IGF-I is accompanied by a variety of undesirable side effects, including hypoglycemia, edema (which can cause Bell's palsy, carpal tunnel syndrome, and a variety of other deleterious conditions), hypophosphatemia (low serum phosphorus), and hypernatermia (excessive serum sodium). Administration of IGF-I as a complex of IGF-I and IGFBP-3 can reduce or eliminate these undesirable side effects (Adams et al., 1996, *Prog. Growth Factor Res.* 6:2–4)

While administration of IGF-I/IGFBP-3 complex may be desirable, the complex, like many proteins, has very limited stability (shelf life) in most formulations. A variety of purportedly stable formulations have been disclosed for IGF-I, either alone or in combination with another proteins (e.g, growth hormone), but the formulations thus disclosed for IGF-I/IGFBP-3 have been unsatisfactory due to poor stability of the proteins. These formulations for binary complex require that the protein be frozen, frequently at very low temperatures (e.g., −70° C.). Freezers, particularly the ultra-low temperature freezers required to maintain −70° C., are uncommon outside of research facilities and are also very expensive. Accordingly, formulations which can be stored at normal refrigerator temperatures or higher while still providing a long shelf life are critical to the commercial development of IGF-I/IGFBP for use as a therapeutic.

A variety of formulations have been disclosed for IGF, particularly IGF-I. For example, U.S. Pat. No. 5,681,814 discloses an IGF-I formulation for use in subcutaneous administration which comprises IGF-I, 2–50 mg/ml of an osmolyte (e.g., sodium chloride), 1–15 mg/ml of a preservative (e.g. benzyl alcohol or phenol) in a buffered in solution at pH 5–5.5. International Patent Application No. WO 97/07816 discloses a liquid IGF-I formulation which comprises IGF-I and mannitol in a buffered solution. However, due to the substantial physico/chemical differences between IGF-I and IGF/IGFBP-3, there is no reasonable expectation that IGF-I formulations will be suitable for IGFBP-3.

It should be noted that, while IGFBP-3 is the most abundant of the IGF binding proteins ("IGFBPs"), at least five other distinct IGFBPs have been identified in various tissues and body fluids. Although these proteins bind IGFs, they originate from separate genes and have distinct amino acid sequences. Unlike IGFBP-3, other circulating IGFBPs are not saturated with IGFs. IGFBP-3 is the only IGFBP which can form the 150 kDa ternary complex with IGF and ALS. However, some of the other IGFBPs have also been suggested for use in combination with IGF-I as therapeutics.

However, despite the advantages of administering IGF-I as a complex with IGFBP-3, little has been disclosed regarding formulations useful for pharmaceutical applications. Bagi et al. (*J. Bone Mineral Res.* 9(8):1301–11311, 1994) disclose the administration of IGF-I/IGFBP-3 to ovariectomized rats. The IGF-I/IGFBP-3 complex was formulated in simple phosphate buffered saline (PBS). Celtrix Pharmaceuticals, Inc. has disclosed the use of IGF-I/IGFBP-3 formulated in acetate buffer (pH 5.5) with 105 mM sodium chloride (NaCl) as the osmolyte. However, this formulation is not ideal for a commercial pharmaceutical formulation, as it does not permit lyophilization of the product.

Lyophilization (freeze drying under controlled conditions) is commonly used for long term storage of proteins. The lyophilized protein is substantially resistant to degradation, aggregation, oxidation, and other degenerative processes while in the freeze dried state. The lyophilized protein is normally reconstituted with water optionally containing a bacteriostatic preservative (e.g., benzyl alcohol). Unfortunately, many preservatives (e.g., benzyl alcohol) are not compatible with proteins, or at least reduce stability. However, the addition of a preservative is currently recommended for drugs which will be administered for periods of 24 hours or more, and this recommendation may become a requirement for drugs sold in the U.S.

Acceptable commercial lyophilized pharmaceutical products must form an acceptable "lyo cake" (mass of lyophilized product). Preferably the lyo cake has a smooth surface and uniform appearance. Lyophilized protein alone rarely makes an acceptable lyo cake, so suitable bulking agents must be added. Generally, carbohydrates such as mannitol, sorbitol, and sucrose are used as bulking agents in lyophilized pharmaceutical products. Additionally, a buffering agent is normally added, particularly in pharmaceutical formulations for proteins such as growth factors and cytokines. The buffering agent is used to control the pH of the formulation when it is in a liquid state (i.e., before lyophilization and after reconstitution) because proteins are normally particularly sensitive to pH fluctuations or extremes.

Accordingly, there is a need in the art for pharmaceutically acceptable formulations that provide high stability for IGF-I/IGFBP-3 drug products.

DISCLOSURE OF THE INVENTION

The inventors have created novel formulations for IGF-I/IGFBP-3 which provide long term stability for IGF-I/IGFBP-3 complex. The formulations of the instant invention are pharmaceutically acceptable.

The inventors have surprisingly found that pharmaceutical formulations of IGF-I/IGFBP-3 complex with very low levels of osmolyte salts are more stable than formulations with high levels of added salts. Additionally, the inventors have found the surprising and unexpected result that omission of pH buffer salts further increases the stability of IGF-I/IGFBP-3 formulations.

In a further surprising and unexpected discovery, the inventors have found that IGF-I/IGFBP-3 formulations with high protein concentrations and having low osmolyte salts and no added pH buffer salts have high stability.

In one embodiment, the formulations of the invention comprise IGF-I/IGFBP-3 complex, a bulking agent, and pH buffer salt. No added osmolyte salt is present in the formulations of this embodiment.

In a further embodiment, the formulations of the instant invention comprise IGF-I/IGFBP-3 complex and a bulking agent. No added osmolyte salts or pH buffer salts are present in the formulations of this embodiment. The formulations of this embodiment are particularly advantageous because they allow the preparation of pharmaceutical formulations which contain very high protein concentrations.

The formulations of the instant invention may be liquid formulations or lyophilized formulations. Optionally, they may also contain a non-ionic surfactant. Liquid formulations may optionally contain a preservative for reducing or eliminating bacterial growth.

BRIEF DESCRIPTION OF THE DRAWINGS

FIG. 1 shows the amino acid sequence (single letter amino acid code) of mature human IGFBP-3 (Ala$_5$) variant.

BEST MODE FOR CARRYING OUT THE INVENTION

The inventors have made a number of surprising and unexpected discoveries which allow the production of commercially and pharmaceutically acceptable, stable IGF/IGFBP formulations. The inventors have found the surprising and unexpected result that elimination of added osmolyte salts increases the stability of IGF-I/IGFBP-3 formulations. Further, and more unexpectedly, the inventors have found that elimination of pH buffer salts increases the stability of IGF-I/IGFBP-3 formulations. The inventors have also surprisingly found that formulations having low levels of osmolyte salts and no added pH buffer salts have increased stability in the presence of benzyl alcohol a commonly used pharmaceutical preservative which frequently promotes aggregation of proteins. Formulations having low osmolyte salts with or without an added pH buffer can be created with high concentrations of IGF-I/IGFBP complex without substantial loss of protein.

Definitions "Insulin-like growth factor" or "IGF" comprises a family of factors, including, but not limited to, IGF-I and IGF-II. The IGFs are polypeptides with molecular weights of about 7.5 kDa. IGF includes naturally occurring IGF-I or IGF-II, analogs or variants thereof (e.g., variants in which one or more of IGF-I's tyrosine residues (i.e., residues 24, 31, or 60) are replaced with non-aromatic residues (i.e., other than tyrosine, phenylalanine or tryptophan), mutants where amino acid residues 49, 50, 51, 53, 55 and 56 are altered (for example, where residues 49–51 are altered to Thr-Ser-Ile or where residues 55–56 are altered to Tyr-Gln) and fusions between IGF-I or IGF-II and other amino acid sequences. IGF may be obtained from natural sources or prepared by recombinant means.

"Insulin-like growth factor binding protein" or "IGFBP", as used herein, is a family of insulin-like growth factor binding proteins which comprises, but is not limited to, IGFBP-1, IGFBP-2, IGFBP-3, IGFBP-4, IGFBP-5 and IGFBP-6. IGFBP may be obtained from natural or recombinant sources.

"Insulin-like growth factor binding protein 3" or "IGFBP-3" refers to one of the members of the IGFBP family. The mature protein is 264 amino acids and, in humans, comprises at least two naturally occurring allelic variant proteins, wherein the fifth amino acid residue of the mature protein is either glycine or alanine (referred to as Gly$_5$ IGFBP-3 and Ala$_5$ IGFBP-3, respectively). When produced by human and other mammalian cells, the protein is post-translationally modified by up to three N-linked glycosylations at three separate sites. When produced in bacteria, the protein is not glycosylated. IGFBP-3 also includes variants of the protein, for example those variants in which the amino acid sites of the normal N-linked glycosylation are altered to another amino acid (sequence variants will be notated throughout the specification as X#Y, where X is the single letter amino acid code for the amino acid residue in the native protein, # is the residue number in the mature protein sequence, and Y is the amino acid to which the residue is changed), particularly aspartate, such as N89D; N109D; N172D; N89D, N109D; N89D, N172D; N109D, N172D; and N89D, N109D, N172D variants or N89X; N109X; N172X; N89X, N109X; N89X, N172X; N109X, N172X; and N89X, N109X, N172X variants. Other variants include alterations at position 116 and 135 where the native sequence aspartate is altered to glutamate (e.g., D116E, D135E and D116E, D135E) or to any other amino acid (e.g., D116X, D135X and D116X, D135X) and variants in IGFBP-3's nuclear localizing sequence (NLS), such as K228E, R230G and K228E, R230G and/or alterations at residues 215, 216 and/or 231. Of course, variant IGFBP-3 may contain more than one variation (e.g., a variant IGFBP-3 may include hydrolysis-resistance variations as well as NLS variations). IGFBP-3 may be produced by purification from natural sources or recombinantly in prokaryotic or eukaryotic host cells, although variants other than naturally occurring allelic variant proteins are preferably produced by recombinant means.

The term "bulking agent" refers to a compound which is pharmaceutically acceptable and which adds bulk to a lyo cake. Acceptable bulking agents include, but are not limited to, carbohydrates such as simple sugars such as dextrose, ribose, fructose and the like, alcohol sugars such as mannitol, inositol and sorbitol, disaccharides including trehalose, sucrose and lactose, naturally occurring polymers such as starch, dextrans, chitosan, hyaluronate, proteins (e.g., gelatin and serum albumin) and glycogen, and synthetic monomers and polymers. Bulking agents for use in the instant invention preferably also act as osmolytes (ie., aid in making the liquid form of the formulation isotonic with normal human serum).

As used herein, the term "osmolyte salt" means salts which are added for the purpose of helping a formulation to become isotonic with normal human serum. Osmolyte salts are normally compounds which are generally regarded as safe for administration to humans, and include sodium chloride, calcium chloride, potassium chloride and the like. Pharmaceutically acceptable osmolyte salts may generally found in the USP (UNITED STATES PHARMACOPEIA, United States Pharmacopeial Convention, Inc., Rockville, Md., 1995).

A "preservative" is a bacteriostatic, bacteriocidal, fungistatic or fungicidal compound which may be added to the formulations of the instant invention to retard or eliminate growth of bacteria or other contaminating microorganisms in the formulations. The preservative should be pharmaceutically acceptable and generally regarded as safe for administration to humans. Examples of preservatives useful in the formulations of the instant invention include benzyl alcohol, phenol, benzalkonium chloride, m-cresol, thimerosol, chlorobutanol, methylparaben, propylparaben and the like. Pharmaceutically acceptable preservatives may generally be found in the USP (Id.). Benzyl alcohol at 0.9–1% (v/v) is a preferred preservative for liquid formulations and reconstituted lyophilized formulations.

As used herein, the term "non-ionic surfactant" refers to a compound which reduces the surface tension of water. Surfactants are sometimes helpful in a number of ways, such as reduction of protein binding to storage and administration devices, for reduction of aggregate formation by proteins and as an aid for the resolubilization of proteins during reconstitution of lyophilized formulations. A surfactant useful in the instant invention will not promote protein denaturation. Examples of surfactants acceptable for use in the instant invention include, but are not limited to polyoxyethylenesorbitan monolaurate (Tween 20), polyoxyethylenesorbitan monooleate (Tween 80), dodecyl poly (oxyethyleneglycol ether)$_{23}$ (Brij 35) and octylphenol poly (ethyleneglycol ether)$_{10}$ (Triton® X-100). Generally, non-ionic surfactants acceptable for use in the compositions of the invention may be found in the USP (Id.).

The term "stable", as used herein in relation to a particular formulation, means that the formulation meets minimum acceptable standards for purity after storage for a specified time under specified conditions. This means that the IGF/IGFBP in the formulation preferably has less than a 30, more preferably less than a 15, percentage point increase in aggregation over the course of one year under normal storage conditions (i.e., approximately 20° C. for a lyo-philized formulation, or refrigerated, frozen or 20° C. for liquid formulations), as measured by size exclusion chromatography (the material is analyzed by SEC and percent aggregation is measured by taking ratio of the peak area of material outside of the main IGF/IGFBP peak to the total peak area). A stable formulation also preferably has less than a 10, more preferably five, percentage point increase degradation over the course of one year under normal storage conditions, as measured by reverse phase HPLC (the material is analyzed by RP-HPLC and percent degradation is measured by taking ratio of the peak area of material outside of the main IGF and IGFBPs peak to the total peak area).

Preferred IGFs include wild-type IGF-I (most preferably recombinant human IGF-I, rhIGF-I) and the variant IGFs, which may be produced by any method known in the art. Preferably, the rhIGF-I is produced recombinantly, utilizing the technology disclosed in International Patent Applications Nos. WO 94/04076 and WO 96/40722. Preferred IGFBPs include recombinant wild-type human IGFBP-3, including naturally occurring allelic variants (particularly the Gly$_5$ and Ala$_5$ allelic variants of wild-type human IGFBP-3) and variants (e.g., the variants at positions 89, 109, 116, 135, 172, 228 and 230) of human IGFBP-3. IGFBPs useful in the instant invention may be produced by any method known in the art, and are preferably produced recombinantly, utilizing the fusion protein technology disclosed in International Patent Applications Nos. WO 94/04076 and WO 96/40722.

Formation of IGF/IGFBP complex is preferably acomplished by simply mixing IGF and IGFBP. In the case of IGF-I and IGFBP-3, the complex forms quickly without any further manipulation. If so desired, the complex may be further purified following complex formation. Such purification may be accomplished by any technique known in the art.

Preferably, the IGF/IGFBP complex for use in the instant formulations has less than 5%, degradation products and less than 15% aggregates.

Normally, the complex is formed with the IGF and IGFBP in an aqueous solution including pH buffer salts and dissolved osmolyte salts (e.g., NaCl). For formation of the formulations of the invention, the dissolved salts, and optionally the pH buffer salts must be removed from the solution. This may be accomplished by any buffer exchange technique known in the art, including, but not limited to, diafiltration, dialysis, reverse osmosis and other ultrafiltration techniques and de-salting by size exclusion chromatography. The protein solution may be directly exchanged into the formulations of the instant invention, or, preferably, it is exchanged into pure water. If the protein solution is exchanged into pure water, the other components of the formulation are added to the water/protein solution and thoroughly mixed. The components of the formulation (e.g., bulking agent) may be added as dry chemicals (which is the form in which most bulking agents and some surfactants are supplied by the manufacturer) or as liquid concentrates.

The formulations of the instant invention contain no added osmolyte salts. Because it is nearly impossible to completely remove salts which are added to buffer solutions during production and purification of IGF and IGFBP, particularly when the formulations are produced in a commercial process, the formulations may not be completely free of osmolyte salts. However, the concentration of osmolyte salts in the formulations of the invention is low, preferably less than 12.5 mM, more preferably less than 2.5 mM, and most preferably less than 1 mM.

In one preferred embodiment, IGF/IGFBP complex is formulated in a pH buffer (i.e., a solution containing buffer salts which can buffer against changes in pH). The pH buffer preferably has a pH of about 5.0 to 7.0, more preferably about 5.5 to 6.5. The IGF/IGFBP may be buffer exchanged into water, followed by the addition of a concentrated solution of pH buffer salts of the desired pH or the addition of dry pH buffer salts to the IGF/IGFBP solution. Alternately, the IGF/IGFBP may be directly buffer exchanged into a pH buffer. Preferably, the IGF/IGFBP is directly buffer exchanged into a pH buffer. The buffer salts may be any buffer salts that are pharmaceutically acceptable, such as sodium phosphate, potassium phosphate, sodium acetate, sodium citrate, and sodium succinate. Preferred buffer salts are sodium citrate and sodium succinate, more preferably sodium succinate. In stability testing experiments, Applicants have surpisingly found that pharmaceutical formulations comprising IGF-I/IGFBP-3 with a pH buffer but lacking added osmolyte salts are more stable than formulations containing added osmolyte salts. In further surprising results, Applicants have found that formulations comprising a succinate buffer at pH 5.5 are more stable than formulations containing citrate and acetate buffers.

In another preferred embodiment of the invention, IGF/IGFBP complex is buffer exchanged into pure water. A bulking agent or agents may be added to the IGF/IGFBP solution to make it isotonic with normal human serum if necessary. Preferably, the bulking agent is mannitol, sorbitol, sucrose, inositol, lactose, dextrose or a mixture of bulking agents. In one preferred embodiment, the bulking agents are mannitol and sucrose, and the bulking agents are added to a total of 6% (w/v), with a preferred ratio of mannitol to sucrose of 3:2 (i.e., 3.6% (w/v) mannitol and about 2.4% (w/v) sucrose). Also contemplated are formulations which are made hypotonic, lyophilized, then reconstituted with a reduced volume of water to create a isotonic formulation of increased protein concentration. For example, IGF-I/IGFBP-3 complex may be formulated in 1.5% mannitol, 1% sucrose at 50 mg/ml protein, lyophilized, then reconstituted to 0.5 times the original volume, to give a reconstituted formulation of 100 mg/ml that is isotonic with human serum. Neither osmolyte salts nor buffer salts are added to the formulations of this embodiment. Applicants have surprisingly found that pharmaceutical formulations comprising IGF-I/IGFBP-3 in mannitol and sucrose which lack any added pH buffer or osmolyte salts are more stable than formulations which contain pH buffers and osmolyte salts. Additionally, Applicants have found that formulations of this embodiment are particularly advantageous because formulations containing very high protein concentrations can be made (see Example 5).

The formulations of the instant invention may be kept as liquid formulations or they may be lyophilized. Liquid formulations are preferably frozen for long term storage. Frozen liquid formulations may be stored in ultra-low freezers (i.e., less than about −70° C.), non-defrosting freezers (i.e., about −20° C.) or defrosting freezers (i.e., cycling between about 5° C. and −15° C.). Preferably, liquid formulations are stored in ultra-low freezers, but storage in non-defrosting freezers or defrosting freezers is acceptable.

Lyophilized formulations are first prepared as liquids, then frozen and lyophilized. The lyophilization process is well known to those of skill in the art, and involves the sublimation of water from the frozen formulation under controlled conditions. Lyophilized formulations may be stored refrigerated or at normal room temperature (e.g., approximately 20° C.). Lyophilized formulations are reconstituted for use by addition of an aqueous solution to redissolve the formulation. Preferably the reconstitution solution is water (e.g., USP WFI, or water for injection) or bacteriostatic water (e.g., USP WFI with 0.9% benzyl alcohol), although solutions containing buffers or other excipients may also be used. Water and bacteriostatic water are preferred reconstitution solutions. Other preservatives may be added to the reconstitution solution, including phenol (preferably about 0.2 to 0.3%), m-cresol (preferably about 0.25–0.3%), thimerosal (preferably about 0.25–0.3%), methylparaben (preferably about 0.25–0.3%), propylparaben (preferably about 0.25–0.3%), chlorobutanol (preferably about 0.5%), and the like.

EXAMPLES

Example 1

Comparison of pH Buffers

Frozen recombinant human (rh) IGF-I/IGFBP-3 (at 10 mg/ml in 50 mM acetate, pH 5.5, and 105 mM NaCl) was thawed and divided into 3 ml samples. One sample was dialyzed against three 500 ml changes of 20 mM sodium succinate 3% mannitol, 2% sucrose, pH 5.5. The second sample was dialyzed against three 500 ml changes of 20 mM sodium citrate, 3% mannitol, 2% sucrose, pH 5.5. After dialysis was complete, the samples were readjusted to 10 mg/ml. The samples were placed in a shelf lyophilizer and allowed to equilibrate at 18° C. for approximately 10 minutes, after which the temperature was reduced to 5° C. for approximately 18 minutes. After equilibration at 5° C., the temperature was quickly reduced to −15° C., where it was held for approximately 12 minutes, then reduced to −35° C., at which point the pressure was reduced in the lyophilizer (200–300 millitorr) and the samples were lyophilized for four hours. The temperature was increased (under vacuum) to 20° C. over 6 hours, then held at 20° C. (under vacuum) for an additional 28 hours.

The two reconstituted samples, plus a control sample of 10 mg/ml IGF-I/IGFBP-3 in 50 mM sodium acetate, 105 mM NaCl, pH 5.5, were incubated at 37° C. for 10 days. At the end of 10 days, the samples were visually inspected, then analyzed by reverse phase high performance liquid chromatography (RP-HPLC) and size exclusion chromatography (SEC). RP-HPLC was performed using a Vydac 4.6×250 mm $C_{18}$ column (5 µm bead size) loaded in 5% acetonitrile, 0.1% trifluoracetic acid (TFA) and eluted with a 26%–34% gradient over 40 minutes. SEC analysis was performed with a Pharmacia Superdex 75 HR 10/30 column run in 50 mM potassium phosphate, 0.5 M NaCl, pH 7.0 at a flow rate of 0.5 ml/min. A sample of rhIGF-I/IGFBP-3 at 10 mg/ml in 50 mM acetate, pH 5.5, and 105 mM NaCl which was kept at −80° C. during the experiment was thawed and used as a control.

RP-HPLC analysis measures the degradation of IGF-I and IGFBP-3 by measuring the ratio of material outside of the main IGF-I and IGFBP-3 peaks to the total material (expressed as percent degradation). The citrate and succinate buffers were approximately equivalent in this test, and also approximately equivalent to the control. Acetate buffer (control) gave 3.6% degradation, while the citrate and succinate formulations were 3.5% and 4.1%, respectively.

SEC analysis showed a great difference between the three samples. SEC analysis is used to measure the formation of protein aggregates, which is expressed at percent aggregate by comparing the material outside of the main IGF-I/IGFBP-3 peak to the total material in the sample. The control had the highest level of aggregate, 6%, while citrate was 5%. Succinate was surprisingly better than the other formulations, with only 2.5% aggregation after 10 days at 37° C.

Example 2 pH Optimization for Formulations Containing pH Buffers 5 ml samples of 10 mg/ml rhIGF-I/IGFBP-3 were dialyzed against 20 mM sodium succinate buffer containing 3% mannitol, 2% sucrose (three changes of 500 ml over 24 hours) at pH 4.5, 5.0, 5.5, 6.0 or 6.5. Following dialysis, protein concentrations were checked by measuring $OD_{276}$, and concentrations were adjusted as necessary to make the samples 10 mg/ml. The pH of each sample was checked to ensure that the pH was within 0.1 pH point of the intended pH, then the samples were sterile filtered and lyophilized as described in Example 1. Sample pH was checked after reconstitution, then the samples were sterile filtered again and aliquots of each were placed at 5° C. and 37° C. for ten days. Stability of the formulation was assayed by RP-HPLC and SEC.

SEC analysis showed that increased aggregation was associated with increased pH. pH 4.5 buffer gave 3.5% aggregation, pH 5 gave 4%, pH 5.5 gave 4.2%, while pH 6 and 6.5 resulted in 5.3% and 7.2% aggregation, respectively.

RP-HPLC analysis showed an opposite trend, with increased degradation generally associated with decreased pH. pH 4.5 gave the highest degradation (6.2%), while the pH 5, 5.5, 6 and 6.5 resulted in 4%, 3.8%, 3.5% and 4.2%, respectively.

Based on these results, pH 5.5 was selected as the best pH for formulations containing a pH buffer.

Example 3

Optimization of pH Buffer Concentration for Formulations Containing pH Buffers 5 ml samples of rhIGF-I/IGFBP-3 were dialyzed against solutions containing 3% mannitol (w/v), 2% sucrose (w/v) and various concentrations of sodium succinate, pH 5.5 (0, 5 mM, 10 mM, 20 mM and 40 mM). Samples were dialyzed for 48 hours in three 500 ml changes of buffer. Following dialysis, protein concentrations were checked by measuring $OD_{276}$, and concentrations were adjusted as necessary to make the samples 10 mg/ml. The pH of each sample was checked to ensure that the pH was within 0.1 pH point of the intended pH, then the samples were sterile filtered and lyophilized as described in Example 1. Sample pH was checked after reconstitution, then the samples were sterile filtered again and aliquots of each were placed at 5° C. and 37° C. for ten days. Stability of the formulation was assayed by RP-HPLC and SEC.

SEC analysis showed a direct correlation between aggregation and succinate buffer concentration. 40 mM succinate resulted in 5.5% aggregation, while the 20 mM, 10 mM, 5 mM and 0 samples resulted in 4.5%, 3.6%, 3.2% and 2.4%, respectively.

RP-HPLC analysis showed that all the samples were equivalent with regards to degradation (3.5–4% degradation), with the exception of the 5 mM sample, which had 7.5% degradation. This "spike" in degradation may be due to a salt optimum for whatever process or enzyme is involved in IGFBP-3 degradation.

These results show that lyophilized formulations without added pH buffer are more stable than formulations with a pH buffer.

Example 4

Formulations Containing High Concentrations of IGF-I/IGFBP-3

30 ml of a 10 mg/ml solution of rhIGF-I/IGFBP-3 was exhaustively dialyzed against 3.6% (w/v) mannitol, 2.4% (w/v) sucrose (formulation solution) then concentrated to 10, 20, and 40 mg/ml by first concentrating the solution by ultrafiltration using an Amicon Centricon® 10 centrifugal ultrafiltration device, testing the concentration by $OD_{276}$, then adjusting the concentration by addition of formulation solution. 10 mg/ml, 20 mg/ml and 40 mg/ml samples of rhIGF-I/IGFBP-3 in formulation solution were lyophilized as described in Example 1, then reconstituted with water or water plus 0.9% benzyl alcohol and sterile filtered. The samples were placed a 37° C. for seven days, then assayed for stability by RP-HPLC and SEC. Assay results are shown in Table 1.

RP-HPLC analysis shows that increasing protein concentration has a minor effect on protein degradation, and that addition of benzyl alcohol does not appear to affect degradation.

SEC analysis showed that increasing protein concentration increased the level of aggregation in the sample. Interestingly, the addition of benzyl alcohol, which normally increases aggregation of protein, and particularly IGF-I/IGFBP-3, had no real effect on aggregation in the mannitol/sucrose formulations without added osmolyte salts or pH buffer.

TABLE 1

| Sample | Degradation | Aggregation |
| --- | --- | --- |
| 10 mg/ml | 1.4% | 1.2% |
| 10 mg/ml + benzyl alcohol | 1.2% | 1.2% |
| 20 mg/ml | 1.9% | 2.1% |
| 20 mg/ml + benzyl alcohol | 1.7% | 2.1% |
| 40 mg/ml | 1.9% | 4.2% |
| 40 mg/ml + benzyl alcohol | 1.3% | 6.1% |

A further experiment was performed, using rhIGF-I/IGFBP-3 concentrated to 75 mg/ml. The protein was first dialyzed extensively against 3.6% mannitol/2.4% sucrose, then concentrated using a stirred cell ultrafiltration device with a 10 kDa cutoff filter. The solution was sterilized by sterile filtration, lyophilized as described above, then reconstituted. The reconstituted protein was assayed to be 75 mg/ml by $OD_{276}$. Samples with and without 0.9% benzyl alcohol were incubated at 37° C. for seven days, then assayed by RP-HPLC and SEC (results are shown below in Table 2).

Extremely high protein concentrations result in increased protein aggregation. Interestingly, although benzyl alcohol had no effect on aggregation or degradation at low protein concentrations, addition of benzyl alcohol at this very high protein concentration did enhance aggregation but not degradation.

TABLE 2

| Sample | Aggregation | Degradation |
| --- | --- | --- |
| 75 mg/ml | 15% | 3.4% |
| 75 mg/ml + benzyl alcohol | 27% | 3.0% |

Example 5

Formulations Containing Very High Concentrations of IGF-I/IGFBP-3 rhIGF-I/IGFBP-3 was exhaustively dialyzed against one of four different formulations: (1) 3.6% mannitol, 2.4% sucrose; (2) 1.5% mannitol, 1% sucrose; (3) 0.525% mannitol, 0.35% sucrose; or (4) water. After dialysis, the solutions were concentrated using a stirred cell concentrator to 50 mg/ml protein concentration.

Samples (1 ml of formulation 1, 2 ml of formulation 2, 4 ml of formulation 3 and 10 ml of formulation 4) were transferred to vials and lyophilized as described in Example 1. The different formulations were designed to yield nominal rhIGF-I/IGFBP-3 concentrations of 50, 100, 200, and 500 mg/ml (calculated final concentrations were actually 49, 96, 187 and 495 mg/ml), respectively. Samples were reconstituted to a net weight of 1 g each and protein concentration was determined by measuring $OD_{276}$, except for formulation 4, which formed a thick syrup which could not be assayed. Purity was measured by SEC in the presence of Brij 35 (the standard, a sample of rhIGF-I/IGFBP-3 which had not been lyophilized, assayed at 98.57% pure in this assay). Results are shown in Table 3

TABLE 3

| Formulation | Nominal Concentration | Expected Concentration | Measured Concentration | Purity by SEC |
|---|---|---|---|---|
| 1 | 50 mg/ml | 49 mg/ml | 50 mg/ml | 98.29% |
| 2 | 100 mg/ml | 96 mg/ml | 96 mg/ml | 98.31% |
| 3 | 200 mg/ml | 187 mg/ml | 186 mg/ml | 97.57% |
| 4 | 500 mg/ml | 495 mg/ml | not measurable | not measurable | pH values were also measured before lyophilization and after reconstitution. Results are shown in Table 4.

TABLE 4

| Formulation | Nominal Concentration | pH Before Lyophilization | pH After Reconstitution |
|---|---|---|---|
| 1 | 50 mg/ml | not determined | 6.88 |
| 2 | 100 mg/ml | 6.91 | 6.87 |
| 3 | 200 mg/ml | 6.62 | 6.80 |
| 4 | 500 mg/ml | 6.60 | not determined |

Osmolality was also measured before lyophilization and after reconstitution using an osmometer. Normal laboratory osmolality values for blood, plasma and serum range from 280–296 mOsm/kg (Merck Manual of Diagnosis and Therapy, R. Berkow ed., 16th edition, at 2581, 1992). Results are shown in Table 5.

TABLE 5

| Formulation | Nominal Concentration | Predicted Osmolality | Measured Osmolality |
|---|---|---|---|
| 1 | 50 mg/ml | 304 mOsm/kg | 309.5 mOsm/kg |
| 2 | 100 mg/ml | 293 mOsm/kg | 297 mOsm/kg |
| 3 | 200 mg/ml | 294 mOsm/kg | 290 mOsm/kg |

In a second experiment to evaluate stability of lyophilized protein in these formulations, rhIGF-I/IGFBP-3 was exhaustively dialyzed against formulation 1, 2 or 3 and lyophilized as described in Example 1. After lyophilization, the samples were (a) reconstituted to 50, 100, or 200 mg/ml ("Time 0") or (b) held at 22° C. or 37° C. for one month ("22° C." and "37° C.", respectively), then reconstituted to 50, 100 or 200 mg/ml nominal concentration. Purity of the samples was assayed by SEC or RP-HPLC (as described in Example 1). rhIGF-I/IGFBP-3 stored at -80° C. served as the control. The results (shown in Tables 6 and 7 for SEC and RP-HPLC, respectively) indicate that formulations 1, 2 and 3 are stable under these conditions, but formulations with low bulking agent concentration (e.g., formulation 3) were slightly less stable due to des(Gly-Pro)IGF-I formation.

TABLE 6

| Formulation | Nominal Concentration | SEC Purity (%) Time 0 | SEC Purity (%) 1 mo. 22° C. | SEC Purity (%) 1 mo. 37° C. |
|---|---|---|---|---|
| Control | 10 mg/ml | 96.7 | 97.5* | 97.5* |
| 1 | 50 mg/ml | not determined | 97.9 | 97.5 |
| 2 | 100 mg/ml | 98.4 | 96.5 | 97.8 |
| 3 | 200 mg/ml | 98.3 | 98.3 | 97.3 |

*Control samples were held at -80° C. during the incubation period.

TABLE 7

| Formulation | Nominal Concentration | HPLC Purity (%) Time 0 | HPLC Purity (%) 1 mo. 22° C. | HPLC Purity (%) 1 mo. 37° C. |
|---|---|---|---|---|
| Control | 10 mg/ml | 99.3 | 99.6* | 99.6* |
| 1 | 50 mg/ml | not determined | 99.5 | 99.6 |
| 2 | 100 mg/ml | 99.4 | 99.4 | 99.6 |
| 3 | 200 mg/ml | 99.4 | 99.3 | 99.4 |

*Control samples were held at -80° C. during the incubation period.

The patents, patent applications, and publications cited throughout the disclosure are incorporated herein by reference in their entirety.

The present invention has been detailed both by direct description and by example. Equivalents and modifications of the present invention will be apparent to those skilled in the art, and are encompassed within the scope of the invention.

We claim:

1. An IGF-I and IGFBP-3 complex formulation, comprising:
   (a) IGF-I/IGFBP-3 complex, wherein said IGF-I is naturally occurring IGF-I, a variant in which one or more tyrosine residue is replaced with a non-aromatic residue, or a variant in which one or more of residues 49, 50, 51, 53, 55, or 56 are altered, and said IGFBP-3 is naturally occurring IGFBP-3, a variant in which one or more of residues 89, 109, or 172 are altered from asparagine to aspartate, a variant in which one or more of positions 116 or 135 are altered from aspartate to glutamate, or a variant in which one or more of residues 228, 230, 215, 216 or 231 is altered;
   (b) a bulking agent, and
   (c) pH buffer salts,
   wherein said formulation contains less than 12.5 mM osmolyte salts.
2. The formulation of claim 1, wherein said bulking agent comprises sorbitol.
3. The formulation of claim 1, wherein said bulking agent comprises mannitol.
4. The formulation of claim 1, wherein said bulking agent comprises sucrose.
5. The formulation of claim 1, wherein said bulking agent comprises mannitol and sucrose.
6. The formulation of claim 5 wherein said mannitol and said sucrose are present in approximately a 3:2 ratio.
7. The formualtion of claim 1, wherein said pH buffer salts comprise sodium succinate.
8. The formulation of claim 7, wherein said pH buffer salts are less than approximately 40 mM.
9. The formulation of claim 7, wherein said pH buffer salts are less then approximately 20 mM.
10. The formulation of claim 7, wherein said pH buffer salts are less than approximately 10 mM.
11. The formulation of claim 1, wherein said formulation has a pH of approximately 5.5 to 6.5.
12. The formulation of claim 1, wherein said formulation further comprises a non-ionic surfactant.
13. The formulation of claim 1, wherin said formulation further comprises a preservative.
14. The formulation of claim 13, wherein said preservative comprises benzyl alcohol.

15. The formulation of claim 1, wherein said formulation is lyophilized.

16. An IGF-I and IGFBP-3 complex formulation, comprising:
(a) IGF-I/IGFBP-3 complex, wherein said IGF-I is naturally occurring IGF-I, a variant in which one or more tyrosine residue is replaced with a non-aromatic residue, or a variant in which one or more residues 49, 50, 51, 53 or 56 are altered, and said IGFBP-3 is naturally occuring IGFBP-3, a variant in which one or more residues 89, 109, or 172 are altered from asparagine to aspartate, a variant in which one or more of positions 116 or 135 are altered from aspartate to glutamate, or a variant in which one or more of residues 228, 230, 215, 216 or 231 is altered; and
(b) a bulking agent;
wherein said formulation contains less than 12.5 mM osmolyte salts and no pH buffer salts.

17. The formulation of claim 16, wherein said bulking agent comprises sorbitol.

18. The formulation of claim 16, wherein said bulking agent comprises mannitol.

19. The formulation of claim 16, wherein said bulking agent comprises sucrose.

20. The fomulation of claim 16, wherein said bulking agent comprises mannitol and sucrose.

21. The formulation of claim 16, wherein said mannitol and said sucrose are present in approximately a 3:2 ratio.

22. The formulation of claim 16, wherein said formulation further comprises a non-ionic surfactant.

23. The formulation of claim 16, wherein said formulation further comprises a preservative.

24. The formulation of claim 23, wherein said preservative comprises benzyl alcohol.

25. The formulation of claim 16, wherein said formulation is lyophilized.

* * * * *

SEQUENCE LISTING

<160> NUMBER OF SEQ ID NOS: 1

<210> SEQ ID NO 1
<211> LENGTH: 264
<212> TYPE: PRT
<213> ORGANISM: Homo sapiens

<400> SEQUENCE: 1

-continued

```
Gly Ala Ser Ser Ala Gly Leu Gly Pro Val Val Arg Cys Glu Pro Cys
 1               5                  10                  15

Asp Ala Arg Ala Leu Ala Gln Cys Ala Pro Pro Pro Ala Val Cys Ala
                20                  25                  30

Glu Leu Val Arg Glu Pro Gly Cys Gly Cys Cys Leu Thr Cys Ala Leu
                35                  40                  45

Ser Glu Gly Gln Pro Cys Gly Ile Tyr Thr Glu Arg Cys Gly Ser Gly
        50                  55                  60

Leu Arg Cys Gln Pro Ser Pro Asp Glu Ala Arg Pro Leu Gln Ala Leu
 65                 70                  75                  80

Leu Asp Gly Arg Gly Leu Cys Val Asn Ala Ser Ala Val Ser Arg Leu
                85                  90                  95

Arg Ala Tyr Leu Leu Pro Ala Pro Pro Ala Pro Gly Asn Ala Ser Glu
                100                 105                 110

Ser Glu Glu Asp Arg Ser Ala Gly Ser Val Glu Ser Pro Ser Val Ser
        115                 120                 125

Ser Thr His Arg Val Ser Asp Pro Lys Phe His Pro Leu His Ser Lys
        130                 135                 140

Ile Ile Ile Ile Lys Lys Gly His Ala Lys Asp Ser Gln Arg Tyr Lys
145                 150                 155                 160

Val Asp Tyr Glu Ser Gln Ser Thr Asp Thr Gln Asn Phe Ser Ser Glu
                165                 170                 175

Ser Lys Arg Glu Thr Glu Tyr Gly Pro Cys Arg Arg Glu Met Glu Asp
                180                 185                 190

Thr Leu Asn His Leu Lys Phe Leu Asn Val Leu Ser Pro Arg Gly Val
                195                 200                 205

His Ile Pro Asn Cys Asp Lys Lys Gly Phe Tyr Lys Lys Lys Gln Cys
210                 215                 220

Arg Pro Ser Lys Gly Arg Lys Arg Gly Phe Cys Trp Cys Val Asp Lys
225                 230                 235                 240

Tyr Gly Gln Pro Leu Pro Gly Tyr Thr Thr Lys Gly Lys Glu Asp Val
                245                 250                 255

His Cys Tyr Ser Met Gln Ser Lys
                260
```